US00PP10649P

United States Patent [19]

Olesen et al.

[11] Patent Number: Plant 10,649

[45] Date of Patent: Oct. 20, 1998

[54] MINIATURE ROSE PLANT NAMED 'POULNOU'

[75] Inventors: L. Pernille Olesen; Mogens N. Olesen, both of Fredensborg, Denmark

[73] Assignee: Poulsen Roser ApS, Fredensborg, Denmark

[21] Appl. No.: 794,881

[22] Filed: Feb. 5, 1997

[51] Int. Cl.[6] ..... A01H 5/00

[52] U.S. Cl. ..... Plt./8.1

[58] Field of Search ..... Plt./8.1

[56] References Cited

PUBLICATIONS

UPOU–ROM, Mar. 1997, Plant Variety Database GTI Jouve Retrieval Software, Citation for POULnou'.

*Primary Examiner*—Howard J. Locker

[57] ABSTRACT

An extremely compact, white flowered, floriferous miniature rose plant which has good shelf life. The new variety is suitable for year round production in glasshouses for commercial pot rose production. The new variety succcessfully propagates from cuttings as well as with traditional budding. The variety has shown to be uniform and stable in the resulting generations from such asexual propagation.

2 Drawing Sheets

SUMMARY OF THE INVENTION

The present invention constitutes a new and distinct variety of miniature rose plant which was developed by artificially pollinating 'POULina,' a variety developed by Poulsen Roser ApS and registered in several European countries, and a un-named seedling. The two parents were crossed in a controlled hybridization progam during the Summer of 1991 and the resulting seed was planted in December, 1991 in a controlled environment. The new variety is named 'POULnou'.

The objective of the hybridization of this rose variety for commercial greenhouse culture was to create a new and distinct variety with:

1. Abundant white flowers with good shelf life;

2. Extremely compact growth, thereby making the variety suitable for production in pot sizes under 3 inches in diameter;

3. Year round flowering under glasshouse conditions;

4. Suitable for production from cutting in pots;

5. Dark green foliage with excellent disease resistance. This combination of qualities was not present in previously available commercial cultivars of this type and distinguish 'POULnou' from all other varieties of which we are aware.

'POULnou' was selected by L. Pernille and Mogens N. Olesen in a rose development program in Fredensborg, Denmark in June, 1992. 'POULnou' was selected as a single plant from the progeny of the crossing of 'POULina' and an un-named seedling.

Asexual reproduction of 'POULnou' cuttings was first done by L. Pernille and Mogens N. Olesen in August, 1992. This initial and subsequent propagations have demonstrated that the characteristics of 'POULnou' are true to type and are transmitted from one generation to the next.

BRIEF DESCRIPTION OF THE DRAWINGS

The accompanying color illustrations show typical specimens of the vegetative growth, leaves, buds, stems, flowers, and a complete plant of 'POULnou'. Specifically illustrated in SHEET 1:

1. Stem or entire plant showing branching and the attachment of leaves, buds, and flowers;

2. Tight bud, ¼ opened bud, and open bloom;

3. Flower petals, detached

4. Sepals, receptacle, and pedicel;

5. flowering stem with terminal and lateral buds, as well as a bare stem exhibiting thorns;

6. Leaves. Specifically illustrated in SHEET 2 is an entire blooming plant in a pot.

DETAILED DESCRIPTION

The following is a detailed description of 'POULnou', as observed in its growth in greenhouses in Fredensborg, Denmark and Half Moon Bay, Calif. and in field nursery in Applegate, Oreg. Descriptions were made from plants treated with growth regulators normally used in the greenhouse production process. The growth regulator Paclobutrazol was applied at 15 ppm weekly for three weeks beginning at a plant age of 6 weeks. The peduncle lengths mentioned may actually be shorter and the foliage color several shades darker than on untreated specimens. Color references are made using The Royal Horticultural Society (London, England) Colour Chart, 1995.

For comparison, the nearest existing rose variety is 'POULtre', a patented variety described and illustrated in U.S. Plant Pat. No. 9,2021 and issued on Dec. 27, 1994. Chart 1 details several physical characteristics of the presently disclosed and the comparison variety.

Chart 1

| Characteristic | 'POULnou' | 'POULtre' |
|---|---|---|
| Flower bud | RHS 155 B of the White Group. | RHS 49C of the Red Group. |
| Flower bloom, upper surface of petals | RHS 155 B of the White Group. | RHS 49C of the Red Group. |
| Sepals | No normally appendaged sepals. | Three normally appendaged sepals. |

Parents: 'POULina'× un-named seedling.

Classification:

*Botanical.*—*Rosa hybrida.*

*Commercial.*—Miniature.

Flower

Blooming cycle: Recurrent.

Flower bud:

*Size.*—13– . mm from ponit of sepal attachment to tip at time when petals begin to unfurl.

*Bud form.*—Elongated, pointed ovoid bud.

*Bud color.*—RHS 155 B of the White Group, at ¼ opening.

*Sepals.*—There are no normally appendaged sepals. Two to three of the sepals have a limited number of thickened hairs on the margins and limited puberscence on the sepal surface. The remaining sepals are covered in fine hairs.

*Peduncle.*—Surface: Smooth. Glabrous. Length: 16–25 mm. Color RHS 143 C of the Green Group. Prickles: Lacking.

*Receptacle.*—Sufrace, glabrous. Shape: Funnel shaped. Size: Small. 3 mm × 4 mm. Color: RHS 143 C of the Green Group.

*Borne.*—One to three buds per flowering stem.

Flower bloom:

*Diameter.*—Small Varying from 25–35 mm.

*Form.*—At opening, the flower bud is high centered. when open, the upper portion of the flower is a flattened convex in form.

*Petalage.*—Double. Average range: 25–30petals.

*Color.*—Upon opening, the upper surface and the reverse side of the petal are RHS 155 B of the White Color Group. After opening, the upper surface and the reverse side of the petal are RHS 155 B of the White Color Group. A small spot of yellow, RHS 4 C of the Yellow Group, exists at the base of the inside and the outside of the petal.

*Petal reflex.*—The most exterior petals are double reflexed, forming a point commonly referred to as quilling. Interior petals are reflexed, turning underwards at the margin.

*Petals.*—Petal edges on some petals weakly undulated. Petal texture is somewhat rough.

*Petaloids.*Commonly lacking.

*Fragrance.*—Very light to light.

*Duration.*—Very long lasting, 14 days on the plant. Petals are white or nearly so from opening until time of petal drop.

Reproductive organs:

*Pollen.*—Limited. Yellow. Yellow-Orange Group.

*Anthers.*—Size: Medium sized for a miniature rose. Quantity: Numerous. Color: Yellow Group 14B upon opening. Browning as flower ages. Visible as flower opens.

*Filaments.*—Color: Yellow-Green 154D. Location: Regular around styles.

*Stigmas.*—Color: Yellow-Green Group 150D. Location: Stigmas are superior in location to the stamens. Visible as flower opens.

*Styles.13* Color: Yellow-Green Group 150D.

*Ovaries.*—Inferior.

Plant

Plant growth: Extremely compact, upright to bushy. When grown as a 6cm pot plant, the average height of the plant itself is 8–10 cm and the average width is 8–10 cm. When grown as a nursery plant on its own roots the average plant height is a 20 –25 cm and the average plant width is 20–25 cm.

Stems:

*Color.*—Young wood: Green. Green Group 143C. Older wood: RHS 143 A of the Green Group.

*Thorns.*—Incidence: Few thorns. Some stiff hairs. Size: Small. To 2.5 mm. in length. Color: Translucent to light green,Yellow-Green Group 145D, drying upon aging to a straw color. Yellow-Orange Group 19D.

Plant foliage:

*Normal number of leaflets on average leaves.*—5 leaflets.

*Leaf size.*—Small.

*Abundance.*—Above average abundance.

*Color.*—Top: Dark green. RHS 147 A of the Yellow Green Group on the uppermost leaves. RHS 147 B of the Yellow Green Group on the lowermost leaves. Bottom: Medium green. RHS 147 C of the Yellow Green Color Group. Older foliage is paler in color than younger foliage. Juvenile growth: The upper leaf surface is Yellow-Green Group 147 A. The lower leaf surface is Yellow Green Group 147 C. Young shoots show little or no anthocyanin coloration.

Plant leaves and leaflets:

*Stipules.*—Present. To 7 mm in length. Bearded. Green Group 147B.

*Petiole.*—Length: 12–15 mm. Underneath: With prickles and stiff hairs.

*Rachis.*—With limited prickles underneath and stiff hairs along upper margin. Green Group 147B.

*Edge.* —Serrated.

*Shape.* —Leaflets are narrowly ovate.

*Leaflets.* —Number: 5 leaflets.

*Other.*—Thin leaflet in cross section. Texture-Upper side: Glossy and smooth.

Disease resistance: Good resistance to mildew, *Botrytis*, blackspot, and rust.

I claim:

1. A new and distinct variety of rose plant of the miniature class, substantially as herein illustrated and described, due to its compact growth, abundant clean white flowers, disease-resistant foliage, its suitability for year round production from cuttings in greenhouses, and its suitability to use as a flowering pot plant.

* * * * *

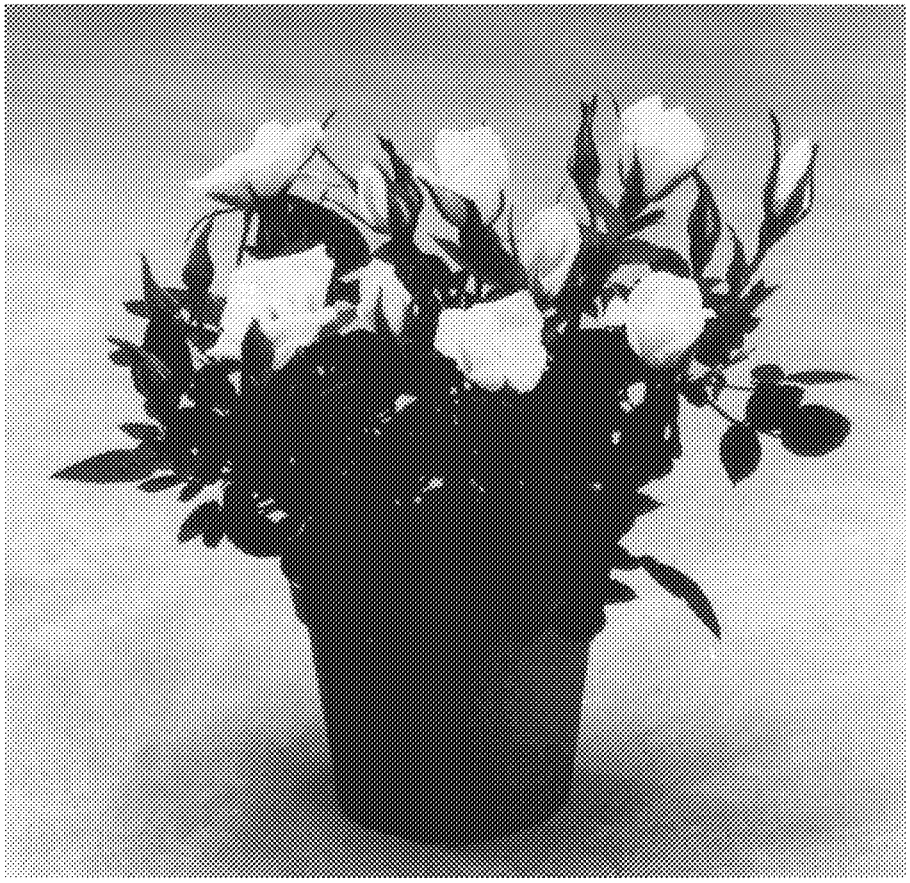

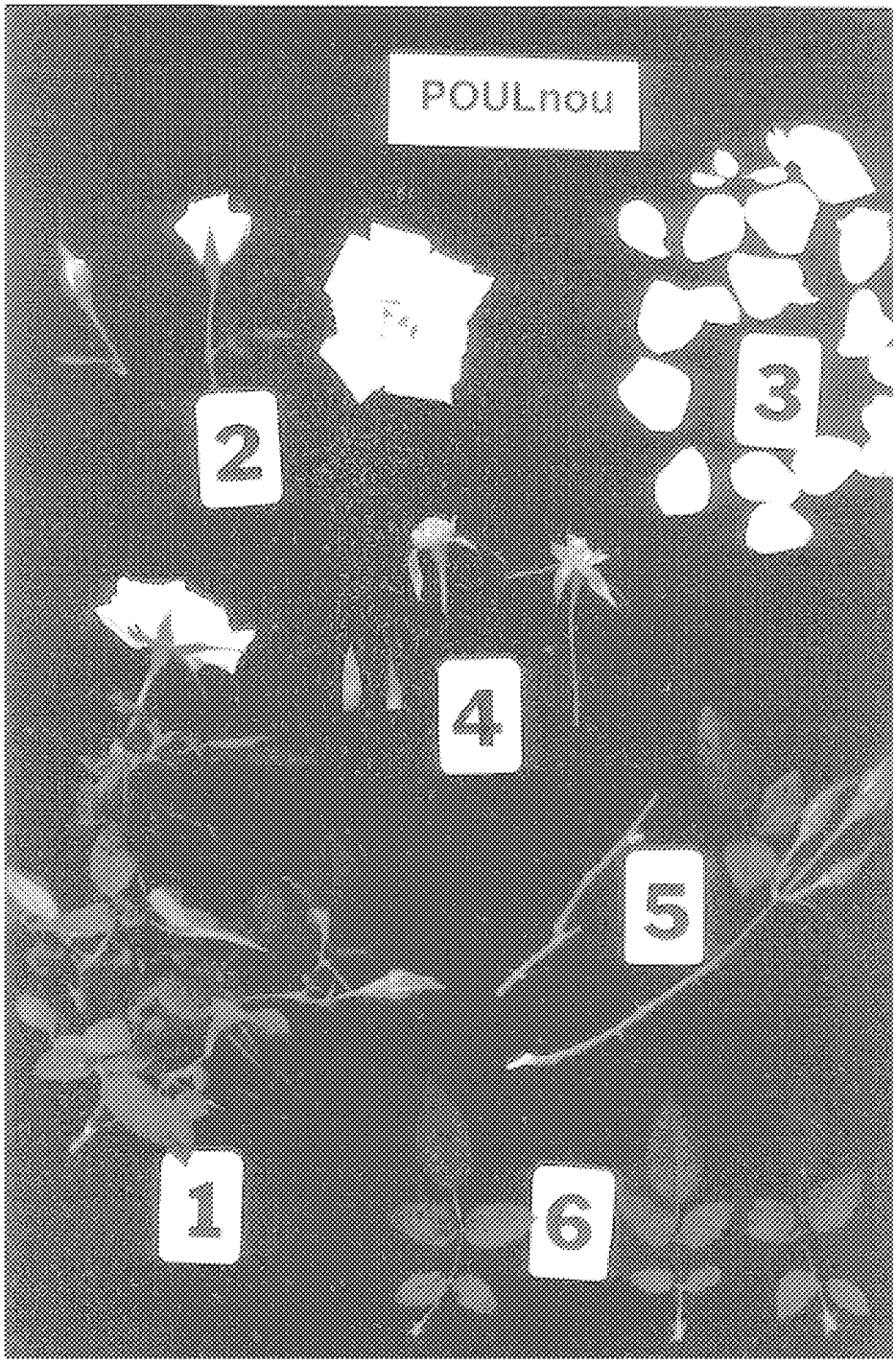
POULnou
1
2
3
4
5
6